United States Patent [19]

Schröder et al.

[11] Patent Number: 4,806,650

[45] Date of Patent: Feb. 21, 1989

[54] PROCESS FOR PREPARING 1-DEOXYNOJIRIMYCIN AND N-DERIVATIVES THEREOF

[75] Inventors: Theo Schröder, Elkhart, Ind.; Mathias Stubbe, Wuppertal, Fed. Rep. of Germany

[73] Assignee: Bayer Aktiengesellschaft, Leverkusen, Fed. Rep. of Germany

[21] Appl. No.: 34,466

[22] Filed: Apr. 2, 1987

[30] Foreign Application Priority Data

Apr. 9, 1986 [DE] Fed. Rep. of Germany ....... 3611841

[51] Int. Cl.$^4$ .................. C12P 19/26; C07D 211/46
[52] U.S. Cl. ................................. 546/242; 435/84; 546/219
[58] Field of Search ................ 546/242, 219; 435/84

[56] References Cited

U.S. PATENT DOCUMENTS

| | | | |
|---|---|---|---|
| 4,246,345 | 1/1981 | Kinast et al. | 435/24 |
| 4,260,622 | 4/1981 | Junge et al. | 514/315 |
| 4,266,025 | 5/1981 | Kinast et al. | 435/84 |
| 4,339,585 | 7/1982 | Matsumura et al. | 546/242 |
| 4,405,714 | 9/1983 | Kinast et al. | 546/242 X |
| 4,429,117 | 1/1984 | Koebernick et al. | 546/219 X |
| 4,611,058 | 9/1986 | Koebernick | 536/18.7 X |

OTHER PUBLICATIONS

McOmie, "Protective Groups in Organic Chemistry", (1973), Plenum Press–London & N.Y.–, pp. 46–52.

*Primary Examiner*—Joseph Paul Brust
*Attorney, Agent, or Firm*—Sprung Horn Kramer & Woods

[57] ABSTRACT

A process for preparing a 1-deoxynojirimycin of the formula

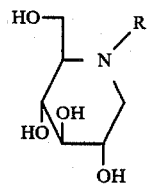

in which R is hydrogen, optionally substituted alkyl or aralkyl, which comprises converting D-glucose to an aminosorbitol

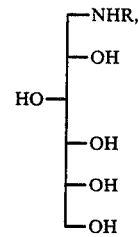

protecting the amino group of the aminosorbitol with an alkalinically detachable group to form the protected compound of the formula

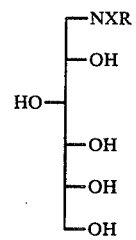

in which X is an alkalinically detachable protective group, microbiologically oxidizing the protected compound to an oxidation product of the formula

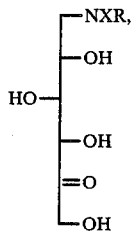

alkalinically splitting off the protective group X to form an aminosorbose of the formula

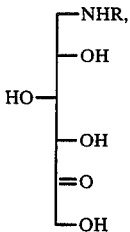

and reducing the aminosorbose.

6 Claims, No Drawings

PROCESS FOR PREPARING 1-DEOXYNOJIRIMYCIN AND N-DERIVATIVES THEREOF

The invention relates to a new process for preparing 1-deoxynojirimycins of the formula

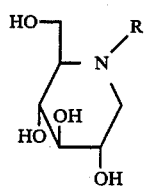   I wherein R denotes hydrogen, optionally substituted alkyl or aralkyl.

The compounds of the formula I are very good α-glucosidase inhibitors and can be used as agents against diabetes, as is known from European Patent Application No. 0,000,947 A 1.

DE-OS (German Published Specification) No. 2,834,122 discloses a process for preparing 1-deoxynojirimycins wherein 1-aminosorbitol II is microbiologically oxidized to

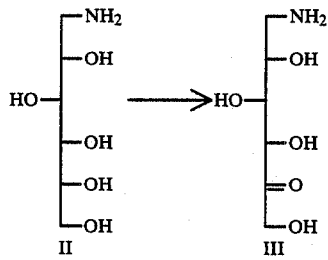

6-aminosorbose III, which can then be hydrogenated to the 1-deoxynojirimycin. However, the yields and volume yields are unsatisfactory. European Patent Application No. 0,049,858 A 2 discloses that aminosorboses IV are obtained by protecting aminosorbitols of the formula V with an acidically detachable group X which is stable to the microbiological oxidation, oxidizing the resulting compounds of the formula VI in a manner known per se to protected aminosorboses VII and subsequently splitting off the protective group with acid.

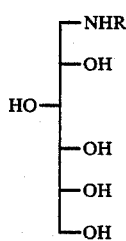   V

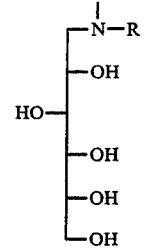   VI

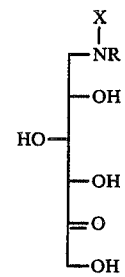   VII

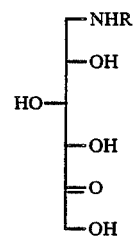   VIII

Hydrogenation of the compounds IV gives deoxynojirimycins I.

It is further known from European Patent Application No. 0,012,278 A 3 that deoxynojirimycins I are obtained when aminosorbitols V are protected with a hydrogenolytically detachable group which is stable in the microbiological oxidation, microbiologically oxidizing the resulting aminosorbitols VI to the protected aminosorboses VII and then, in one step, hydrogenolytically splitting off the protective group and hydrogenating the resulting aminosorboses intermediates to deoxynojirimycins. However, in this last step a large amount of a valuable noble metal catalyst is required.

All the other known processes for preparing deoxynojirimycins require may steps and expensive purification processes. They are cited in European Patent Application Nos. 0,012,278 A 3 and 0,000,947 A 1.

It has now been found that compounds of the formula I can be obtained in a very simple way and in high yields without requiring any purification of the aminosorboses VII or a large amount of catalyst. To this end, D-glucose X

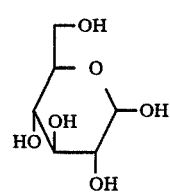   X

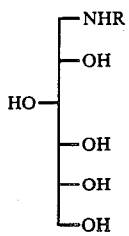  (XI)

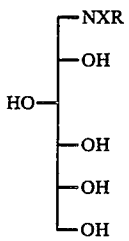  (XII)

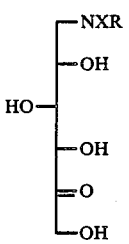  (XIII)

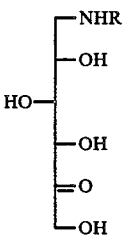  (XIV)

is converted in a manner known per se into the aminosorbitols XI where R has the abovementioned meaning, and the amino group is protected with an alkalinically detachable group which is stable in the subsequent microbiological oxidation. The resulting compounds XII are microbiologically oxidized in a manner known per se to the protected aminosorboses XIII. Then the protective groups are split off alkalinically, and the resulting aminosorboses are reduced in a manner known per se, catalytically or with complex hydrides, to the deoxynojirimycins of the formula I.

The invention therefore relates to a process for preparing 1-deoxynojirimycins of the formula (I)

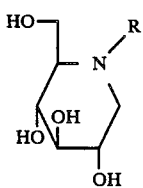  (I)

wherein R denotes hydrogen, optionally substituted alkyl or aralkyl, characterized in that D-glucose is converted in a manner known per se into aminosorbitols (XI)

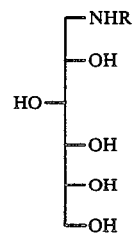  (XI)

the amino group in (XI) is protected with an alkalinically detachable group which is stable in the subsequent microbiological oxidation, the protected compounds of the formula (XII)

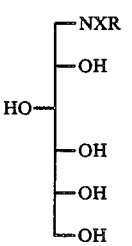  (XII)

wherein X stands for an alkalinically detachable protective group, are microbiologically oxidized to compounds of the formula (XIII)

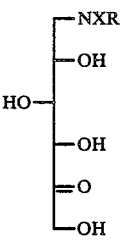  (XIII)

and the protective groups are subsequently alkalinically split off, affording the compounds of the formula (XIV)

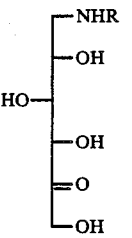  (XIV)

and the aminosorboses thus obtained are reduced in a manner known per se, catalytically or with complex hydrides, to the deoxynojirimycins of the formula I where R has the abovementioned meaning.

The radical R preferably denotes hydrogen of $C_1$–$C_{10}$-alkyl, in particular $C_1$–$C_4$- alkyl. These alkyl radicals can be substituted by up to 3 OH or $C_1$–$C_4$-alkoxy radicals.

Suitable substituents for alkyl also include phenyl, which in turn can be substituted by up to 3 halogens, in particular chlorine and fluorine, OH, nitro, amino, $C_1$–$C_4$-alkylamino, $C_1$–$C_4$-trialkylamino, CN, $C_1$–$C_4$-alkyl, $C_1$–$C_4$-alkoxycarbonyl, carboxyl or phenyl.

Furthermore, R also denotes phenyl, which can be substituted as indicated above, or aralkyl having 6 to 10 carbon atoms in the aryl part and 1 to 4 carbon atoms in the alkyl part, it being possible for the alkyl part and the aryl part to be substituted by the substituents indicated above for alkyl and phenyl.

Very particular preference is given to the compounds described in the examples, in connection with their methods of preparation.

Very particularly preferably R denotes hydrogen, $C_1$–$C_{10}$-alkyl or hydroxyethyl.

Suitable protective groups X are all groups which can be split off alkalinically and are stable under the conditions of the microbiological oxidation. Examples which may be mentioned are the following protective groups: formyl, acetyl, mono-, di- and trihalogenoacetyl such as chloroacetyl, dichloroacetyl, trichloroacetyl, trifluoroacetyl, benzoyl and hydroxyl-, alkoxy-, halogen- and nitro-substituted benzoyl, methoxycarbonyl, tert.-butyloxycarbonyl, but any other protective group from the huge number of alkalinically detachable protective groups is in principle also suitable for carrying out the process according to the invention. Particular preference is given to the formyl, the dichloroacetyl and the trichloroacetyl protective groups. The preparation of the intermediate products XII is effected in the case of the amide protective groups in a manner known per se from the amines XI and the corresponding carboxylic acid esters or carboxylic acid anhydrides in suitable solvents.

The compounds XII are readily crystallizing compounds, in particular in the case of R=H, which frequently even crystallize out when hot, in the course of the preparation, and thus can be obtained in high purity in a simple manner.

The preparation can be effected not only with alkyl carboxylates but also with aryl carboxylates, as well as with the symmetrical and mixed carboxylic acid anhydrides. Suitable solvents are all inert organic solvents and water as well as mixtures thereof. Examples which may be mentioned are the alcohols such as methanol, ethanol, isopropanol and tert.-butanol, ketones such as acetone and methyl isobutyl ketone, carboxyamides such as dimethylformamide and N-methylpyrrolidone and dimethyl sulphoxide.

Particular preference is given to methyl and ethyl carboxylates and also to water, methanol, ethanol, dimethylformamide and N-methylpyrrolidone as solvents.

The introduction of the alkoxycarbonyl protective group is effected in a manner known per se, by reacting the corresponding dialkyl pyrocarbonate in aqueous solvent mixtures.

The compounds of the formula XIII can be very simply prepared in a manner known per se from the compounds of the formula XII by oxidizing the protected aminosorbitols XII in aqueous solutions with suitable microorganisms (for example Gluconobacter oxidans). The compounds thus obtained are either readily water-soluble or can be separated from the microorganisms by extraction with suitable solvents.

To split off the protective groups, the solution of XIV thus obtained is optionally diluted or concentrated and treated with a concentrated or dilute base. The course of the splitting off can be monitored chromatographically, and depending on the nature and amount of the base used and also the protective group is complete within a few minutes to a few hours. The splitting off can be effected at temperatures of 0° C. to 60° C., preference being given to a range from 15° to 30° C.

A suitable base is any hydroxide or carbonate, provided it is sufficiently soluble in water.

Preference is given to the ammonium, alkali metal and alkaline earth metal hydroxides and also tetraalkylammonium hydroxides.

It is also possible to use basic ion exchangers as bases. Particular preference is given strongly basic ion exchangers such as, for example, Lewatit ® MP 500 OH form. The exchanger resins can be not only gellike but also macroporous. The use can be effected by the batch method, i.e. adding the exchanger to the solution of XIV, or even in columns.

The alkaline splitting off of the protective groups leads in a virtually uniform reaction to the aminosorboses XIV. This result is extremely surprising in the light of the state of the art, since it is known from Paulsen et al. Chem. Ber. 100, 802 (1967) that aminosorboses XIV, in particular those where R=H, are only stable in strongly acid aqueous solutions and even in the neutral range rapidly decompose, for example to the pyridine derivative XV. Furthermore, it is also surprising that the aminosorboses XIV can nonetheless be reduced in a simple manner and high yields to the compounds I.

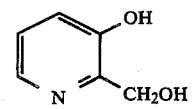
(XV)

The reduction of the aminosorboses XIV can be effected in a manner known per se. It can be effected for example by catalytic hydrogenation over suitable catalysts of the type described in European Patent Application No. 49,858 A 2. However, preference is given to the reduction with complex boron hydrides. Particular preference is given to sodium boronate, sodium cyanoborohydride, dialkylaminoboranes and basic anion exchangers in the $BH_4^\ominus$ form. Very particular preference is given to sodium boronate $NaBH_4$, dimethylaminoborane $BH_4H(CH_3)_2$ and the ion exchangers Lewatit M 500, M 600 AP 246, MP 500, MP 600 in the $BH_4^\ominus$ form. The use of complex boron hydrides is known and described in European Patent Application EP No. 055,431 A 1. Expediently the reduction is carried out immediately after the protective group has been split off. Before the start of the reduction the pH value of the solution can be set to values between pH 1 and pH 14. Preference is given to the range between pH 4–13.

A particularly simple procedure results when an alkali-stabilized sodium boronate solution is added to the alkaline solution of the elimination reactants. This reduction in the alkaline medium further has the advantage that virtually no boronate decomposes to form hydrogen, as is the case with reduction in the acid and neutral range, and can form dangerous detonating gas mixtures with air.

This particular advantage of the alkaline elimination makes it possible to reduce the aminosorboses XIII in tubular reactors which are packed with basic ion exchangers in the $BH_4^\ominus$ form.

To isolate and purify the deoxynojirinycins I, it is possible, depending on the process variant and material properties, either to crystallize directly from the optionally concentrated preparative solution or to adsorb the deoxynojirimycins onto an acid ion exchanger and to elute with optionally dilute acid, salt, ammonia or amine solution, or to adsorb onto an anion exchanger in the $OH^{\ominus}$ form, or, however, to chromatograph over suitable ion exchangers (for example Lewatit TSW 40 $Na^{\oplus}$ form), silica gel or silinated silica gel, to concentrate in each case the product-containing solutions and to recrystallize from suitable solvents.

Suitable ion exchangers are in principle all weakly and strongly acid, as well as weakly and strongly basic types.

Preference is given to strongly acid and strongly basic ion exchangers.

The principle of the process according to the invention is not restricted to the microorganisms mentioned in the examples, but on the contrary the process according to the invention can also be carried out with other oxidizing strains which are found by the skilled worker in nature or are obtainable from depositary institutions.

EXAMPLE 1

Preparation of N-formyl-1-amino-1-deoxy-D-glucitol. A suspension of 1-aminosorbitol(1-amino-1-deoxy-D-glucitol) (200 g) in methanol (800 ml) and methyl formate (102 ml) is refluxed for 3 hours. This gives in a short time a clear solution, from which the product begins to crystallize immediately. This is followed by cooling, and the product is isolated by filtration. Yield: 212 g (92% of theory)

Melting point: 139°–141° C.

EXAMPLE 2

Preparation of N-dichloroacetyl-1-amino-1-deoxy-D-glucitol.

The preparation is effected from 1-aminosorbitol and methyl dichloroacetate analogously to Example 1.

Yield: 86% of theory.

Melting point: 167°–169° C.

EXAMPLE 3

Preparation of N-trichloroacetyl-1-amino-1-deoxy-D-glucitol.

The preparation is effected from 1-aminosorbitol and methyl dichloroacetate analogously to Example 1.

Yield: 83% of theory.

$C_8H_{14}Cl_3NO_6$ (326.6): Calculated: C 29.4%, H 4.3%, N 4.3%, Cl 32.6%, Found: C 29.7%, H 4.3%, N 4.4%, Cl 32.2%.

EXAMPLE 4

Preparation of N-formyl-N-methyl-1-amino-1-deoxy-D-glucitol.

The preparation is effected from N-methyl-1-amino-1-deoxy-D-glucitol and methyl formate analogously to Example 1.

Yield: 85% of theory.

Melting point: 119°–121° C.

EXAMPLE 5

Preparation of N-formyl-N-hydroxyethyl-1-amino-1-deoxy-D-glucitol.

The preparation is effected from N-hydroxy-1-amino-1-deoxy-D-glucitol and methyl formate analogously to Example 1. After the reaction has ended, the reaction mixture is evaporated to dryness in vacuo.

Yield: 93% of theory of syrup.

EXAMPLE 6

Preparation of N-dichloroacetyl-N-hydroxyethyl-1-amino-1-deoxy-D-glucitol.

The preparation is effected from N-hydroxy-ethyl-1-amino-1-deoxy-D-glucitol and methyl dichloroacetate analogously to Example 1.

Yield: 96% of theory of syrup.

EXAMPLE 7

Preparation of N-formyl-6-amino-6-deoxy-L-sorbose.

To a suspension of 40 g of Gluconobacter oxidans spp. suboxidans (DSM 50049) in 1 l of tap water, brought to pH 4.5 with phosphoric acid, are added at 32° C. and 700 rpm with venting of 3 l of air/hour 200 g of N-formylaminosorbitol, followed 4 hours later by a further 200 g of N-formylaminosorbitol. After 22 hours the reaction has ended, the cells are centrifuged off and discarded. The product is isolated as an oil by concentrating in vacuo.

EXAMPLE 8

Preparation of N-dichloroacetyl-6-amino-6-deoxy-L-sorbose.

To a suspension of 40 g of Gluconobacter oxidans ssp. suboxidans (DSM 50049) in 1 l of tap water, brought to pH 4.5 with phosphoric acid, are added at 32° C. and 700 rpm with venting of 3 l of air/hour 20 g of N-dichloroacetylaminosorbitol. The reaction has ended after 10 hours, and the cells are then centrifuged off, washed twice with 100 ml of methanol each time and discarded. The methanol extracts are combined with the aqueous supernatant and concentrated to dryness in vacuo.

EXAMPLE 9

Preparation of N-trichloroacetyl-6-amino-deoxy-L-sorbose.

The reaction and isolation is effected in the case of a reaction duration of 24 hours and a substrate amount of 55 g of the corresponding sorbitol as described in Example 8.

EXAMPLE 10

Preparation of N-formyl-N-methyl-6-amino-6-deoxy-L-sorbose.

The reaction and isolation is effected in the case of a reaction duration of 16 hours and a substrate amount of 10 g of the corresponding sorbitol as described in Example 8.

EXAMPLE 11

Preparation of N-formyl-N-hydroxyethyl-6-amino-6-deoxy-L-sorbose.

The reaction and isolation is effected in the case of a reaction duration of 45 hours and a substrate amount of 150 g of the corresponding sorbitol, added in 5 portions of 50 g each in the course of 25 hours, as described in Example 8.

EXAMPLE 12

Preparation of N-dichloroacetyl-N-hydroxyethyl-6-amino-6-deoxy-L-sorbose.

The reaction and isolation is effected in the case of a reaction duration of 28 hours and a substrate amount of 80 g of the corresponding sorbitol as described in Example 8.

EXAMPLE 13

Preparation of deoxynojirimycin from N-formyl-6-amino-6-deoxy-L-sorbose.

To the solution of N-formyl-6-amino-6-deoxy-L-sorbose (from 0.4 mol of N-formylaminosorbitol) in water (400 ml) is added a solution of sodium hydroxide (20 g) in water (24 ml), which is followed by two hours of stirring at 20° C. A solution of sodium boronate (3.8 g) in water (40 ml), which has been stabilized with a few drops of 45% strength sodium hydroxide solution, is then added, which is followed by 1 hour of stirring at 20° to 25° C. After addition of acetone (10 ml) the solution is poured onto a column of strongly acid ion exchanger (1 1 Lewatit SP 112 H⊕ form), and washed with demineralized water (two column volumes), and the deoxynorjirimycin is eluted out with 6% strength aqueous ammonia. The product-containing solutions are concentrated to dryness in vacuo and the product is crystallized from ethylene glycol monomethyl ether.

Yield: 33.3 g 51.0% relative to starting N-formylaminosorbitol.

Melting point: 193°-194° C.

EXAMPLE 14

Preparation of 1-deoxynojirimycin from N-formyl-6-amino-6-deoxy-2-sorbose.

To the solution of formylaminosorbose (from 0.4 mol of N-formylaminosorbitol) in water (400 ml) is added barium hydroxide octahydride, which is followed by 2 hours of stirring at 20° C. A solution of dimethylaminoborane (20 g) in water (200 ml) is then added, which is followed by a further hour of stirring. The pH value of the solution is adjusted to 6.8–7.2 with sulphuric acid (30% strength), and precipitated barium sulphate is filtered off. The filtrate is concentrated and chromatographed over silica gel (mobile phase acetonitrile:water:25% strength aqueous ammonia 4:1:1 v/v/v). The product-containing solutions are concentrated to dryness in vacuo, and the residue is recrystallized from water/ethanol.

Yield: 50.2% relative to starting N-formylaminosorbitol.

Melting point: 192°-193° C.

EXAMPLE 15

Preparation of deoxynojirimycin from N-formyl-6-amino-6-deoxy-L-sorbose.

To the solution of N-formylaminosorbose (from 0.4 mol of formylaminosorbitol) in water (400 ml) is added Lewatit MP 500 OH⊖ form (1 l), which is followed by one hour of stirring at 20° C. Lewatit MP 500 BH4⊖ form (200 ml) is then added, which is followed by a further hour of stirring at 20° C. The ion exchanger is filtered off and product residues are completely washed out with water. The filtrate is evaporated in vacuo, and the residue crystallized from ethylene glycol monomethyl ether.

Yield: 53.3% relative to a starting N-formylaminosorbitol.

Melting point: 192°-193° C.

EXAMPLE 16

Preparation of 1-deoxynojirimycin from N-dichloroacetyl-6-deoxy-L-sorbose.

The preparation is effected from N-dichloroacetylaminosorbose analogously to Example 13.

Yield: 53.9% relative to starting N-dichloroacetylaminosorbitol.

Melting point: 192°-193° C.

EXAMPLE 17

Preparation of deoxynojirimycin from N-dichloroacetyl-6-amino-6-deoxy-L-sorbose.

The preparation is effected from N-dichloroacetylaminosorbose analogously to Example 14. The reducing agent used is Lewatit MP 500 BH4⊖ form (200 ml) in place of dimethylaminoborane.

Yield: 53.3% relative to starting N-dichloroacetylaminosorbitol.

Melting point: 192°-193° C.

EXAMPLE 18

Preparation of deoxynojirimycin from N-trichloroacetyl-6-amino-6-deoxy-L-sorbose.

The preparation is effected from N-trichloroacetylaminosorbose analogously to Example 13.

Yield: 57% of theory, relative to N-trichloroacetylaminosorbitol.

Melting point: 193°-194° C.

EXAMPLE 20

Preparation of N-methyl-1-deoxynojirimycin from N-formyl-N-methyl-6-amino-6-deoxy-L-sorbose.

The preparation is effected from N-formyl-N-methylaminosorbose analogously to Example 13.

Yield: 46% of theory, relative to starting N-formyl-N-methylaminosorbose.

Melting point: 152°-153° C.

EXAMPLE 21

Preparation of N-hydroxyethyl-1-deoxynojirimycin from N-formyl-N-hydroxyethyl-6-amino-6-deoxy-L-sorbose.

The preparation is effected from N-formyl-N-hydroxyethylaminosorbose analogously to Example 13.

Yield: 42% of theory, relative to starting N-formyl-N-hydroxyethylaminosorbitol.

EXAMPLE 22

Preparation of N-hydroxyethyl-1-deoxynojirimycin from N-dichloroacetyl-N-hydroxyethyl-6-amino-6-deoxy-L-sorbose.

The preparation is effected from N-dichloroacetyl-N-hydroxyethylaminosorbose analogously to Example 13.

Yield: 47% of theory, relative to starting N-dichloroacetyl-N-hydroxyethylaminosorbitol.

It is understood that the specification and examples are illustrative but not limitative of the present invention and that other embodiments within the spirit and scope of the invention wil suggest themselves to those skilled in the art.

We claim:

1. A process for preparing a 1-deoxynojirimycin of the formula

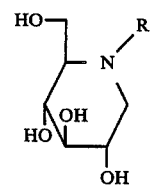

in which R is hydrogen, alkyl, carbocyclic aryl or carbocyclic aralkyl, which comprises converting D-glucose to an aminosorbitol of the formula

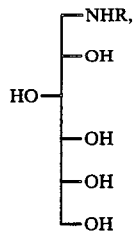

protecting the amino group of the aminosorbitol with an alkalinically detachable group to form the protected compound of the formula

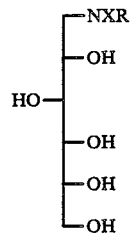

in which X is an alkalinically detachable protective group, microbiologically oxidizing the protected compound to an oxidation product of the formula

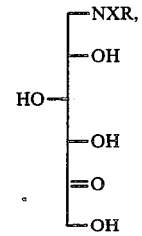

alkalinically splitting off the protective group X to form an aminosorbose of the formula

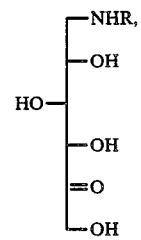

and reducing the aminosorbose thereby to obtain the 1-deoxynojirimycin.

2. A process according to claim 1, in which R is hydrogen, $C_1$–$C_{10}$-alkyl or phenyl.

3. A process according to claim 1, in which R is hydrogen or $C_1$–$C_4$-alkyl.

4. A process according to claim 1, in which X is formyl, dichloroacetyl or trichloroacetyl.

5. A process according to claim 1, wherein the alkalinical splitting off is effected with an alkali metal, alkaline earth metal or an ammonium hydroxide or a basic ion exchanger.

6. A process according to claim 1, wherein reduction of the aminosorbose is effected with hydrogen and a hydrogenation catalyst or with a complex boron hydride.

* * * * *

UNITED STATES PATENT AND TRADEMARK OFFICE
CERTIFICATE OF CORRECTION

PATENT NO. : 4,806,650
DATED : Feb. 21, 1989
INVENTOR(S) : Schroder et al.

It is certified that error appears in the above-identified patent and that said Letters Patent is hereby corrected as shown below:

Col. 5, line 2        Insert --$C_1$-$C_4$-alkoxy,-- after "alkyl,"
Col. 6, line 11       Insert --to-- after "given"

Signed and Sealed this

Twenty-eighth Day of November 1989

*Attest:*

JEFFREY M. SAMUELS

*Attesting Officer*    *Acting Commissioner of Patents and Trademarks*